United States Patent [19]

Twerdochlib

[11] Patent Number: 4,833,453
[45] Date of Patent: May 23, 1989

[54] MONITORING OF MOVABLE COMPONENTS

[75] Inventor: Michael Twerdochlib, Oviedo, Fla.

[73] Assignee: Westinghouse Electric Corp., Pittsburgh, Pa.

[21] Appl. No.: 152,273

[22] Filed: Feb. 4, 1988

[51] Int. Cl.$^4$ .............................. G08B 21/00
[52] U.S. Cl. ............................... 340/540; 73/587; 137/554; 340/679; 340/686
[58] Field of Search .......... 340/540, 679, 683, 686; 73/587; 137/554

[56] References Cited

U.S. PATENT DOCUMENTS

| | | | |
|---|---|---|---|
| 3,373,526 | 3/1968 | Parkin | 49/25 |
| 3,914,754 | 10/1975 | Kirk | 137/553 |
| 4,417,235 | 11/1983 | Del Grande | 340/531 |
| 4,459,850 | 7/1984 | Hyanova et al. | 73/587 |
| 4,524,620 | 6/1985 | Wright et al. | 73/587 |
| 4,590,963 | 5/1986 | Gardner et al. | 137/554 |

FOREIGN PATENT DOCUMENTS

| | | | |
|---|---|---|---|
| 2478255 | 9/1981 | France | 137/554 |
| 0017079 | 7/1982 | Japan | 137/554 |
| 0068581 | 4/1983 | Japan | 137/554 |

*Primary Examiner*—Glen R. Swann, III

[57] ABSTRACT

A method and device for monitoring the operation of a component which is located in a sealed enclosure and is movable into a selected operating position in response to an activating signal uses the steps of: generating a short-duration acoustic signal in the enclosure in response to the movement of the component into the selected operating position; sensing the acoustic signal at the exterior of the sealed enclosure; and determining the time relationship between the activating signal and the acoustic signal. The acoustic signal is generated by an element which is carried by or moveable with the component and which generates the acoustic signal by striking an interior surface of the enclosure when the component moves into the selected operating position.

12 Claims, 1 Drawing Sheet

U.S. Patent      May 23, 1989      4,833,453
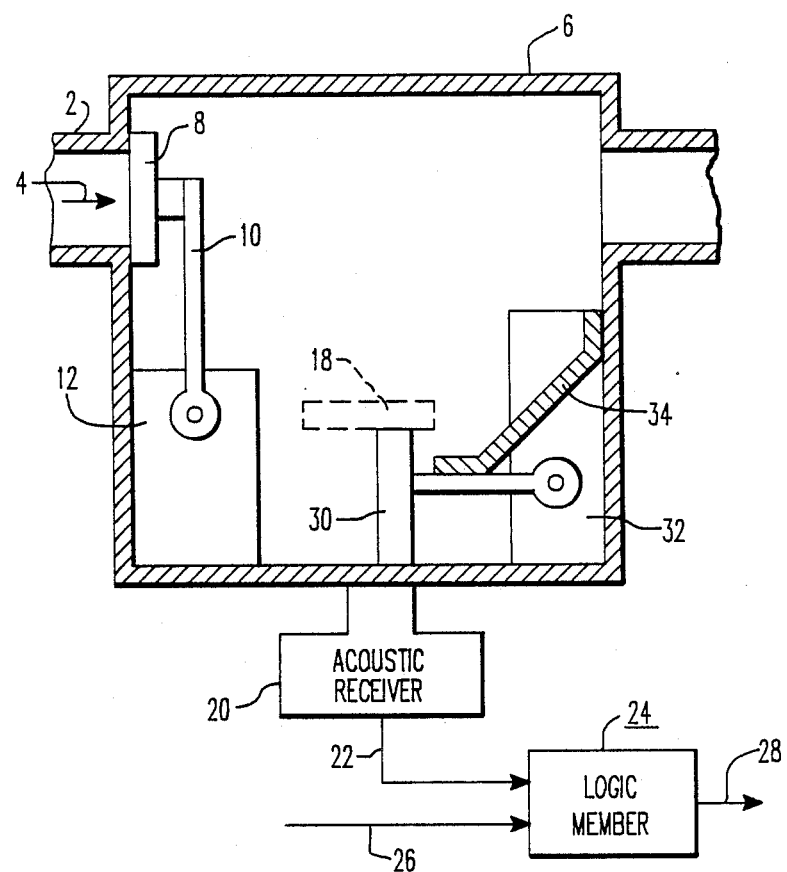

4,833,453

MONITORING OF MOVABLE COMPONENTS

BACKGROUND OF THE INVENTION

The present invention relates to a method and apparatus for monitoring the operation of a component which is located in a sealed enclosure.

Many types of systems include movable components which are not accessible from outside the system and whose operational status cannot be readily determined. This is frequently the case in fluid-flow systems which, by their nature, contain flow-control components that are not accessible from the exterior, at least while the system is in operation.

It is known to monitor the operating state of components in a fluid-flow system indirectly by monitoring the fluid pressure upstream and downstream of the component, and/or the velocity of fluid-flow past the component. Such monitoring systems are relatively costly and are themselves prone to failure and malfunction. Moreover, each such monitoring device communicates with the fluid-flow path through an opening which must itself be sealed.

SUMMARY OF THE INVENTION

It is an object of the present invention to monitor the operating state of movable components in a sealed enclosure in a simplified manner.

Another object of the invention is to monitor the operating state of such components without penetrating the enclosure.

A further object of the invention is to monitor the operating state of such components using a monitoring arrangement which is simple and inexpensive.

The above and other objects are achieved, according to the present invention, by a method for monitoring the operation of a component which is located in a sealed enclosure and is movable into a selected operating position in response to an activating signal, comprising:
  generating a short duration acoustic signal in the enclosure in response to the movement of the component into the selected operating position;
  sensing the acoustic signal at the exterior of the sealed enclosure; and
  determining the time relationship between the activating signal and the acoustic signal.

The objects of the invention are further achieved by a device for monitoring the operation of a component which is located in a sealed enclosure and is movable into a selected operating position in response to an activating signal, which device comprises:
  means for generating a short duration acoustic signal in the enclosure in response to the movement of the component into the selected operating position;
  sensing means acoustically coupled to the sealed enclosure and located at the exterior of the enclosure for sensing the acoustic signal ; and
  monitoring means connected to the sensing means for determining the time relationship between the activating signal and the acoustic signal.

BRIEF DESCRIPTION OF THE DRAWING

The sole FIGURE is a partly cross-sectional, partly schematic view of a preferred embodiment of a monitoring device according to the present invention.

DESCRIPTION OF THE PREFERRED EMBODIMENTS

The FIGURE shows a pipeline 2 for conducting a fluid in the direction 4, the pipeline including a housing 6 containing a one-way valve component 8. Component 8 is supported by pivot arm 10 pivotally mounted on a base 12 fixed in housing 6.

An actuating mechanism (not shown) of any suitable, known type is connected to pivot arm 10 and is responsive to an electrical signal defining the flow-blocking state so as to rotate pivot arm 10 to bring valve component 8 into the position, shown in solid lines in the FIGURE, in which component 8 blocks flow along path 4. In certain systems, the valve component will not be brought to the fully closed position in response to a closing signal. When that signal disappears, or a signal defining the flow establishing state is produced, pivot arm 10 pivots to bring valve component 8 to the open position depicted by the broken outline 18.

According to the invention, an acoustic receiver 20, which may include an acoustic-to-electrical signal transducer and an amplifier, is acoustically coupled to pipeline 2 or housing 6 in that the acoustic sensor of receiver 20 is placed in contact with the outer wall of pipeline 2 or housing 6 at a location where the generated acoustic signal, or impulse, will be clearly received. Receiver 20 is operative to produce an output signal on line 22 representative of acoustic impulses transmitted through the portion of the wall of pipeline 2 or housing 6 to which receiver 20 is acoustically coupled. Line 22 is connected to a logic member 24 which additionally receives the above-mentioned flow-blocking signal via a line 26.

According to one possible implementation of the invention, the creation of a flow-blocking signal moves pivot arm 10 in a manner such that the closing movement produces an impact of valve component 8 against a seating surface associated with pipeline 2 sufficient to apply to receiver 20 an acoustic signal producing a discernable pulse signal on line 22. In this case, it may be preferable to mount receiver 20 at a location close to the flow-blocking position of component 8.

The duration of the flow-blocking signal on line 26 is selected to be of a sufficient length to at least partially overlap the resulting signal pulse appearing on line 22 in response to the closing movement of valve component 8. This partial overlap will be interpreted by logic member 24 as a proper valve closing operation, so that no fault signal will be emitted on output line 28. If, on the other hand, a flow-blocking signal appearing on line 26 is not associated with an at least partially overlapping signal on line 22, this constitutes an indication of a faulty valve closing operation, and logic member 24 will supply an alarm signal on line 28. Thus, logic member 24 functions, in effect, as a logic ANDNOT member, and could be constituted by such a member, possibly together with appropriate amplifying and pulse shaping circuitry.

In many cases, the closing movement of valve component 8 will not directly produce a sufficient acoustic signal. For example, in high flow systems, an initial closing signal will only move component 8 partially to its closed position, full closure occurring at a later time after flow has otherwise been blocked. In this case, in further accordance with the invention, housing 6 is equipped with an auxiliary acoustic signal generating element which operates in response to movement of valve component 8 to its flow-blocking position. In the illustrated embodiment, this auxiliary element is a pivotal member 30 supported on a base 32 and biased, as by a leaf spring 34, into the illustrated position. In the illustrated embodiment, spring 34 is fixed to member 30 and is slidable relative to the interior wall of housing 6.

When pivot member 30 is in the illustrated position and valve component 8 is in the position 18, component 8 and member 30 will be in contact.

At least in the region where these two parts are in contact, one of them is made of a magnetic material and the other of a magnetizable material so that a magnetic attraction exists therebetween.

When, upon appearance of a flow-blocking signal, valve component 8 begins to move toward its flow-blocking position, member 30 will be pivoted in opposition to its associated biassing force until a point is reached at which the magnetic contact between valve component 8 and member 30 is broken, either because the biassing force exceeds the magnetic attraction force or because member 30 has reached the end of its permissable travel path. After contact has been broken, member 30 is driven by its associated biassing force to strike housing 6 and thus produce an acoustic signal which is processed by receiver 20. The resulting output signal is then interpreted in logic member 24 in the same manner as the signal described above.

It can thus be seen that the present invention offers, in addition to being structurally simple, reliable, and inexpensive, the possibility of monitoring the complete component operation in that an alarm signal will be produced regardless of the cause of component malfunction. Thus, in the case of the valve illustrated in the FIGURE, an alarm signal will be produced regardless of whether malfunction is due to failure of the associated actuator to respond to the valve closing signal, failure of the linkage between the actuator and pivot arm 10, blockage of arm 10, or separation of component 8 from arm 10. In addition, when receiver 20 responds directly to impact of component 8 against its valve seat, incomplete valve closing will be detected.

If the activating signal employed to move valve component 8 to its valve-closing position has such a short duration that it can terminate before a proper acoustic signal is generated, then the activating signal can be employed to produce a pulse having a suitably long duration, and it will be this pulse which is applied to line 26. Conversely, if the activating signal has an unacceptably long duration, e.g. if the activating signal remains present as long as component 8 is in its valve closed position, then the leading edge of each activating signal can be used to generate a pulse of suitable duration, which is applied to line 26. In any event, according to the invention, each activating signal should serve to provide on line 26 a pulse having a duration which is sufficiently long to assure that it will overlap with the corresponding acoustic impulse, but short enough to assure that a spurious acoustic impulse will not produce a faulty indication of proper component operation.

While the illustrated embodiment relies on magnetic coupling between member 30 and component 8, it would equally be possible to establish a releasable mechanical connection therebetween.

According to further embodiments of the invention, acoustic receiver 20 can be thermally isolated from pipeline 2 or housing 6, for example by means of a standoff, so that the monitoring of components in a system conducting high temperature or low temperature fluids can be effected with a relatively inexpensive acoustic receiver.

Since a monitoring operation according to the present invention requires the detection of only relatively strong acoustic impulses, the acoustic receiver can be a relatively inexpensive device and its output signal need not be subjected to any type of measurement, analysis or shaping.

While the invention has been described with reference to the monitoring of a nonreturn valve, it will be appreciated that the monitoring method and devices according to the present invention can be employed to monitor the proper operation of any enclosed component which is to be moved to a defined position by an activating signal. The use of a separate movable member will be dictated in part by the nature of the component to be monitored and under consideration of whether that component, in its normal operation, will itself produce an acoustic pulse of sufficient magnitude.

It will be understood that the above description of the present invention is susceptible to various modifications, changes, and adaptations, and the same are intended to be comprehended within the meaning and range of equivalents of the appended claims.

What is claimed is:

1. A method for monitoring the operation of a component which is located in a sealed enclosure and is movable into a selected operating position in response to an activating signal, comprising:
   generating a short-duration acoustic signal in the enclosure in response to the movement of the component into the selected operating position;
   sensing the acoustic signal at the exterior of the sealed enclosure; and
   determining the time relationship between the activating signal and the acoustic signal.

2. A method as defined in claim 1 wherein said step of generating an acoustic signal is carried out by causing the component to impact against the enclosure.

3. A method as defined in claim 1 wherein said step of generating an acoustic signal is carried out by displacing a movable element within the enclosure to a displaced position in response to movement of the component toward the selected operating position, and then causing the movable element to move from the displaced position to impact against the enclosure.

4. A method as defined in claim 3 wherein said step of displacing is carried out by establishing a magnetic attraction between the movable element and the component, and permitting the movable element to be displaced with the component during a portion of the movement of the component toward the selected operating position.

5. A method as defined in claim 4 wherein said step of causing the movable element to move comprises applying to the movable element a biassing force in the direction toward the enclosure.

6. A method as defined in claim 1 wherein said step of determining comprises producing an alarm signal when an acoustic signal does not occur in at least a selected time interval after initiation of an activating signal.

7. A device for monitoring the operation of a component which is located in a sealed enclosure and is movable into a selected operating position in response to an activating signal, comprising:
   means for generating a short-duration acoustic signal in the enclosure in response to the movement of the component into the selected operating position;

sensing means acoustically coupled to the sealed enclosure and located at the exterior of the sealed enclosure for sensing the acoustic signal; and monitoring means connected to said sensing means for determining the time relationship between the activating signal and the acoustic signal.

8. A device as defined in claim 7 wherein said component constitutes said means for generating an acoustic signal.

9. A device as defined in claim 7 wherein said means for generating an acoustic signal comprise a movable element mounted within the enclosure for movement to a displaced position in response to movement of the component toward the selected operating position, and means for causing said movable element to move from the displaced position to impact against the enclosure.

10. A device as defined in claim 9 further comprising means associated with at least one of said movable element and said component for establishing a magnetic attraction therebetween for permitting said movable element to be displaced with said component during a portion of the movement of said component toward the selected operating position.

11. A device as defined in claim 10 wherein said means for causing the movable element to move comprises biassing means coupled to said movable element for applying to said movable element a biassing force in the direction toward the enclosure.

12. A device as defined in claim 7 wherein said monitoring means comprise means for emitting an alarm signal when an acoustic signal does not occur in at least a selected time interval after initiation of an activating signal.

* * * * *